United States Patent [19]

Schellhammer et al.

[11] 4,447,651
[45] May 8, 1984

[54] 1,4-BIS-(4-CHLORO-2-METHOXYSTYRYL)-BENZENE

[75] Inventors: Carl-Wolfgang Schellhammer, Bergisch Gladbach; Bernhard Wehling, Cologne, both of Fed. Rep. of Germany

[73] Assignee: Bayer Aktiengesellschaft, Leverkusen, Fed. Rep. of Germany

[21] Appl. No.: 370,697

[22] Filed: Apr. 22, 1982

[30] Foreign Application Priority Data

May 9, 1981 [DE] Fed. Rep. of Germany ....... 3118525

[51] Int. Cl.$^3$ .................................... C07C 43/263
[52] U.S. Cl. ........................... 568/645; 252/301.21; 524/369
[58] Field of Search .................. 568/645; 252/301.21

[56] References Cited

U.S. PATENT DOCUMENTS

| 3,177,153 | 4/1965 | Pommer et al. | 568/645 X |
| 3,294,570 | 12/1966 | Pommer et al. | 117/33.5 |
| 3,991,049 | 11/1976 | Siegrist et al. | 252/301.35 |

FOREIGN PATENT DOCUMENTS

| 1043501 | 9/1966 | United Kingdom | 568/645 |

*Primary Examiner*—Bernard Helfin
*Attorney, Agent, or Firm*—Sprung, Horn, Kramer & Woods

[57] ABSTRACT

1,4-Bis-(4-chloro-2-methoxystyryl)-benzene is highly suitable for whitening polymeric substances, in which use it is distinguished, for example, by a good yield and a pleasant shade.

1 Claim, No Drawings

1,4-BIS-(4-CHLORO-2-METHOXYSTYRYL)-BENZENE

It is known that compounds of the bis-styrylbenzene series are valuable whiteners for various types of macromolecular materials (compare German Patent Specification No. 1,273,812).

However, numerous compounds of this substance class which have been described by way of example in the literature do not always satisfy the technological requirements which high quality whiteners have to meet nowadays. This is true in particular for certain intended uses, such as, for example, the mass-colouring of thermoplastics.

It has now been found that 1,4-bis-(4-chloro-2-methoxystyrl)-benzene stands out from the large number of known bis-styrylbenzenes on account of a particularly interesting spectrum of properties. A property to be emphasised above all is the suitability of this compound for whitening thermoplastic materials, in which use it is distinguished, inter alia, by a high light-fastness, a high yield and a pleasant colour shade.

Examples of suitable thermoplastic substances are polyesters, vinyl polymers, acrylic polymers, allyl polymers, polyamides, polyolefines and other commercially available polymeric products and polycondensates.

In addition to these fully synthetic polymers, natural and semi-synthetic products are suitable, such as, for example, cellophane, cellulose acetate and cellulose butyrate and mixtures thereof with the synthetic products mentioned above.

The new whitener is also suitable for optically brightening thermosetting resins which are not coloured or coloured only to a small extent, such as, for example, melamine resins.

The new bis-styrylbenzene compound is particularly highly suitable for whitening plasticised PVC, polystyrene, ABS polymers, polyethylene and polypropylene.

The whitener can be added to these macromolecular substances in various ways.

For example, it can be admixed to spinning melts and spinning solutions of fibre- and film-forming polymers.

In some cases it is more advantageous to admix the whitener to polymerisable or polycondensable monomers or to precondensates before the polymerisation However, it is also possible to incorporate the whitener subsequently into macromolecular substances in a customary manner.

The amounts used are 0.001–0.1 percent by weight, relative to the material to be brightened.

The preparation of the whitener can be carried out by various processes which are in themselves known (for example German Patent Specifications Nos. 1,108,219 and 1,112,072 and British Patent Specification No. 1,043,501).

One process is characterised in that 2 mols of a dialkyl 4-chloro-2-methoxybenzylphosphonate (alkyl being for example methyl or ethyl) are condensed with terephthalaldehyde.

In another process, 4-chloro-2-methoxybenzaldehyde (2 mols) are reacted with a dialkyl p-xylylene-$\alpha,\alpha'$-bis-phosphonate.

The two methods are advantageously carried out in a suitable organic solvent, such as, for example, dimethylformamide, in the presence of an alkaline condensating agent (for example KOH or NaOCH$_3$).

PREPARATION EXAMPLE

Bromination of 4-chloro-2-methoxytoluene by means of N-bromosuccinimide in boiling carbon tetrachloride in the presence of dibenzoyl peroxide produces 4-chloro-2-methoxybenzyl bromide as a colourless liquid which has a boiling point of 140°–145° C./13 mm Hg. Reaction of this compound with triethyl phosphite in boiling xylene turns it into diethyl 4-chloro-2-methoxybenzylphosphonate; this is a colourless, viscous liquid which has a boiling point of 132° C./0.1 mm Hg.

36 g (0.2 mol) of a 30% strength sodium methylate solution are added dropwise under an atmosphere of nitrogen to a mixture of 29.3 g (0.1 mol) of diethyl 4-chloro-2-methoxybenzylphosphonate, 6 g, (0.049 mol) of terephthalaldehyde and 100 ml of N,N-dimethylformamide. This mixture is stirred for 1 hour at room temperature and for 3 hours at 60° C. The content of the flask is then poured onto ice water, the mixture is neutralised, and the material precipitated is filtered off with suction and dried after washing with water. 18 g of a yellow crude product are obtained which is dissolved and reprecipitated from xylene/Tonsil. 1,4-Bis-(4-chloro-2-methoxystyryl)-benzene is then in the form of small yellow needles which melt at 188°–192° C. A solution of the substance in N,N-dimethylformamide has an absorption maximum at 372.9 nm, and the molar extinction is about 60,000.

USE EXAMPLES

Example 1

102 parts of a polyvinyl chloride composition consisting of 70 parts of polyvinyl chloride, 30 parts of a plasticiser, for example dioctyl phthalate, and 2 parts of a stabiliser are rolled for about 5 minutes at 150° C. on a two-roll mill together with 0.01 part of the whitener mentioned in the preparation example and drawn out to produce films. In order to produce matt films 2.5 parts of titanium dioxide are added to the composition prior to the rolling. Plasticised PVC films which have an outstanding white effect are obtained in this manner.

Example 2

0.05 part of the whitener mentioned in the preparation example is mixed with 100 parts of polystyrene granules having a titanium dioxide content of 2% and the mixture is injection-moulded at 230° C. on a screw injection-moulding machine to give small sample plates. The small plates obtained show an excellent brightening effect.

Example 3

If the polystyrene granules are replaced by ABS granules having a titanium dioxide content of 4% and in other respects the procedure given in Use Example 2 is followed, small ABS sample plates are obtained which have an outstanding white effect.

Example 4

If the polystyrene granules are replaced by a polypropylene homopolymeric product having a titanium dioxide content of 2% and the procedure described in Use Example 2 is followed in other respects, small PP sample plates are obtained which show an outstanding white effect.

We claim:

1. 1,4-Bis-(4-chloro-2-methoxystyryl)-benzene.